United States Patent [19]

Pieniak et al.

[11] 4,450,026
[45] May 22, 1984

[54] METHOD OF FORMING A CONFORMABLE GARMENT WITH "KILLED" ELASTIC PORTIONS

[75] Inventors: Heinz A. Pieniak, Chicago; Virginia L. Repke, Oak Forest, both of Ill.

[73] Assignee: Johnson & Johnson Baby Products Company, New Brunswick, N.J.

[21] Appl. No.: 391,326

[22] Filed: Jun. 23, 1982

Related U.S. Application Data

[60] Division of Ser. No. 106,336, Dec. 21, 1979, Pat. No. 4,337,771, which is a continuation-in-part of Ser. No. 872,860, Jan. 27, 1978, abandoned.

[51] Int. Cl.³ .................. A61F 13/16; B32B 31/08; B32B 31/18
[52] U.S. Cl. .................. 156/164; 156/229; 156/291; 156/301; 156/303; 156/324; 604/385
[58] Field of Search .............. 156/163, 164, 229, 290, 156/291, 300, 301, 324, 303; 604/366, 358, 393, 385

[56] References Cited

U.S. PATENT DOCUMENTS

| | | | |
|---|---|---|---|
| 2,502,772 | 4/1950 | Winstead | 156/163 |
| 3,639,917 | 2/1972 | Althouse | 2/270 |
| 3,819,401 | 6/1974 | Massengale et al. | 156/229 |
| 3,860,003 | 1/1975 | Buell | 604/385 |
| 3,912,565 | 10/1975 | Koch et al. | 156/290 |
| 4,050,462 | 9/1977 | Woon et al. | 604/385 |
| 4,081,301 | 3/1978 | Buell | 156/164 |
| 4,300,967 | 11/1981 | Sigl | 156/164 |
| 4,325,372 | 4/1982 | Teed | 604/385 |

*Primary Examiner*—Jerome W. Massie
*Attorney, Agent, or Firm*—Martha A. Michaels

[57] ABSTRACT

A disposable diaper having improved fit about the legs and/or waist of the wearer and having reinforced corners for enhanced securement of the diaper about the wearer is disclosed. Improved fit and reinforcement are obtained by an elongated, inherently elastic ribbon member positioned along at least one margin of the diaper. The ribbon member is secured to the diaper so as to provide an elastic region at a central portion of the margin and a unitary, relatively inelastic reinforced region in a corner portion of the diaper.

10 Claims, 13 Drawing Figures

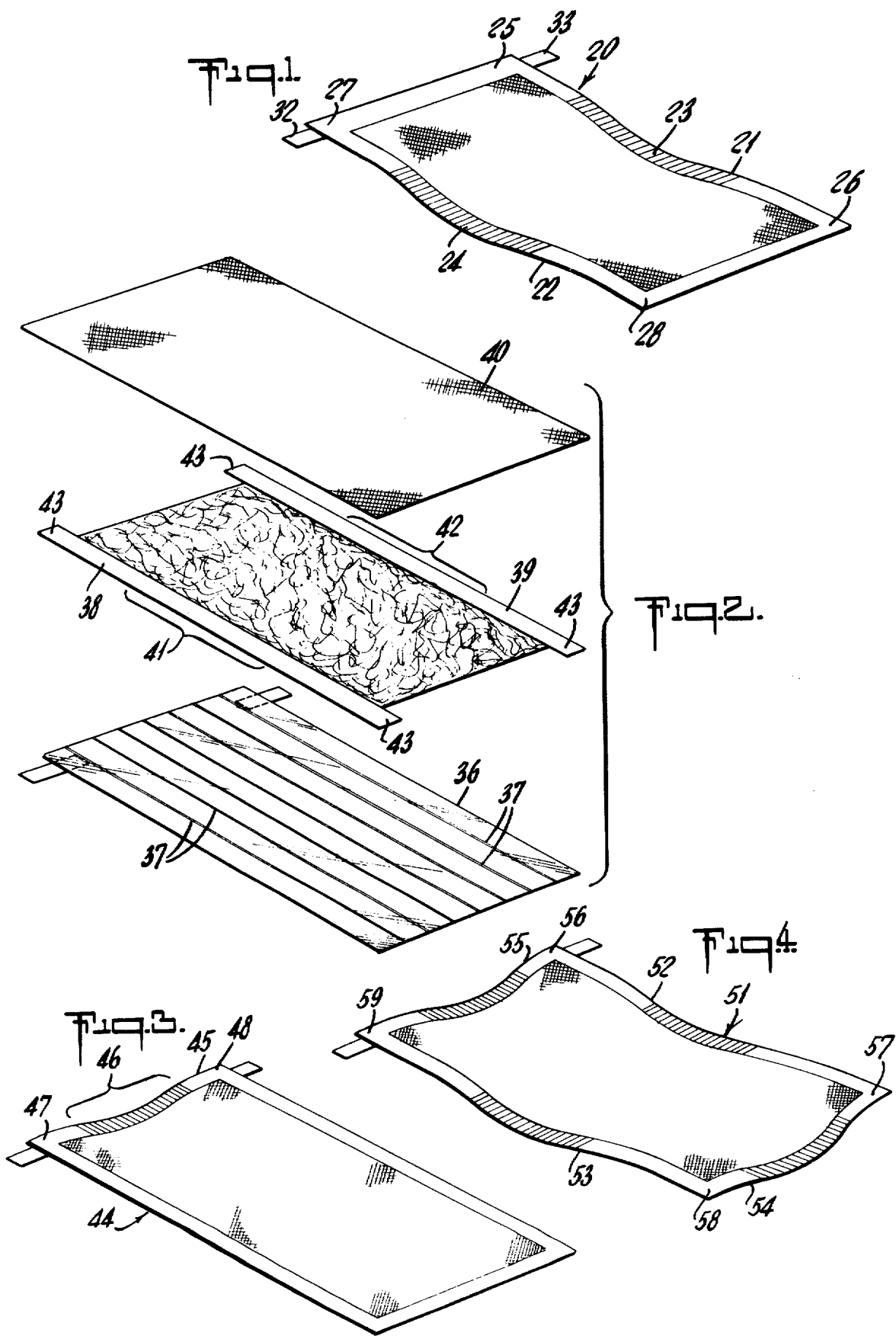

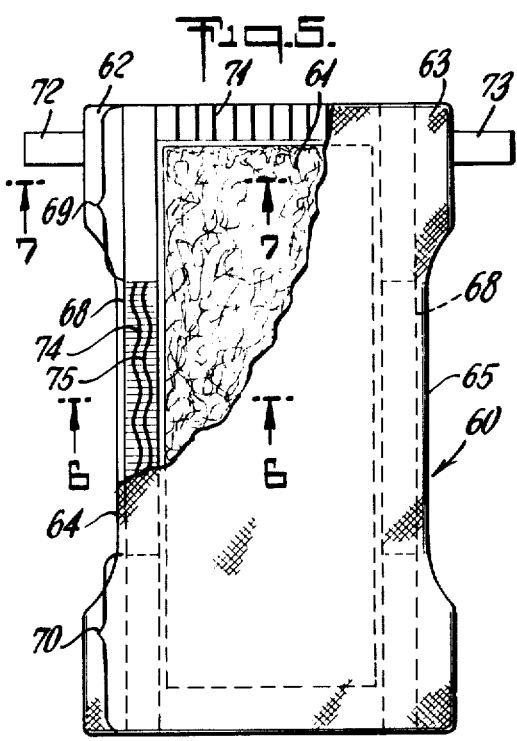
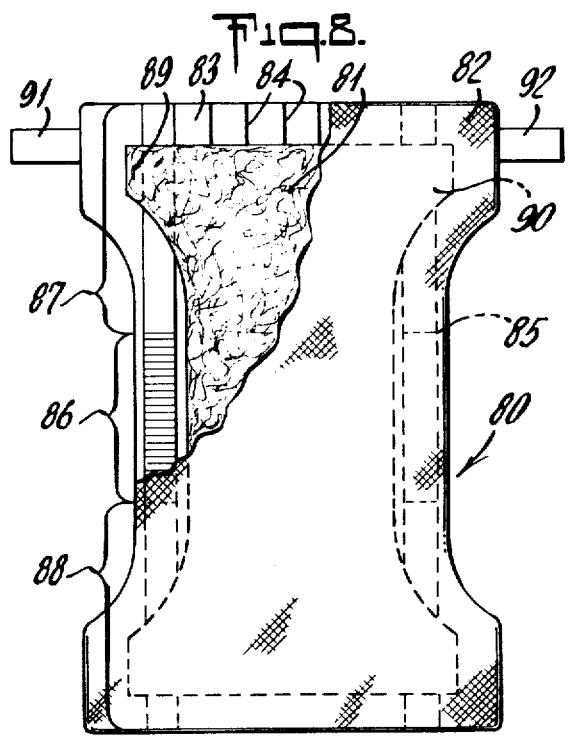
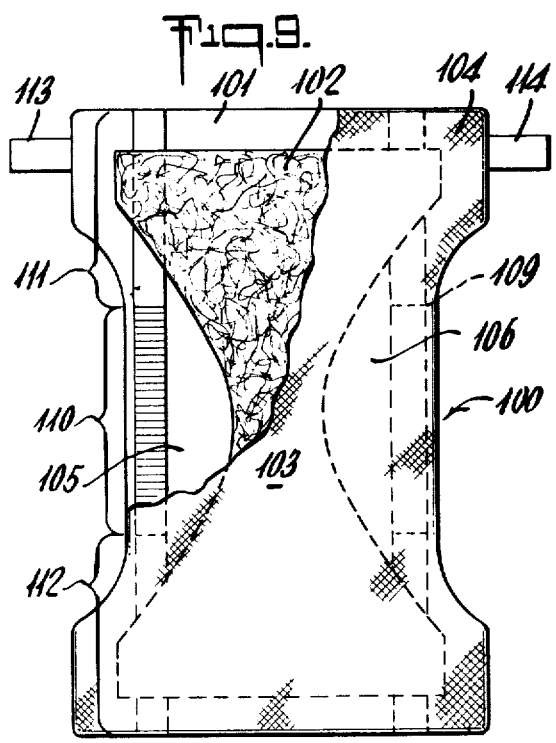
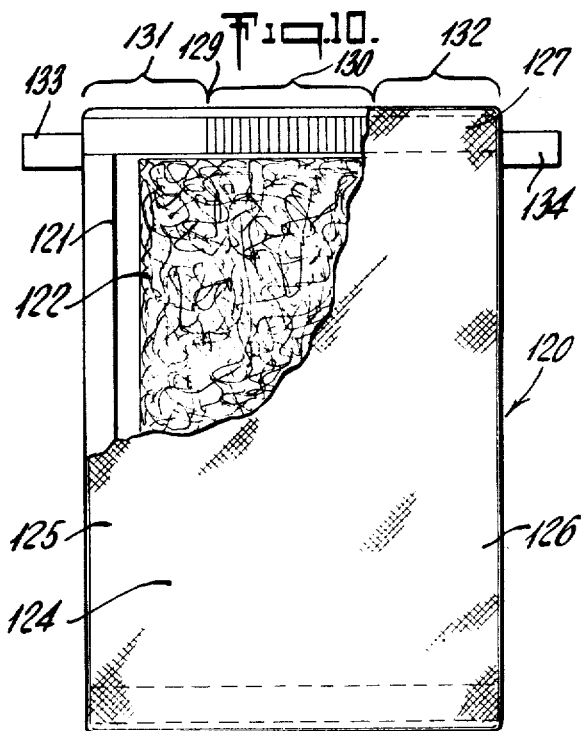
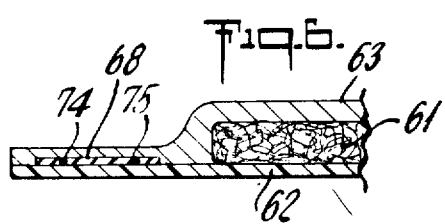
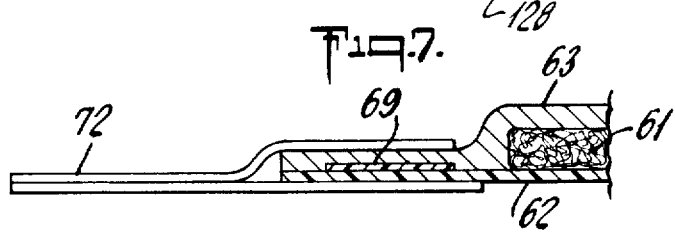

METHOD OF FORMING A CONFORMABLE GARMENT WITH "KILLED" ELASTIC PORTIONS

This application is a division of application Ser. No. 106,336 filed Dec. 21, 1979, now U.S. Pat. No. 4,337,771; which was a continuation-in-part of application Ser No. 872,860 filed Jan. 27, 1978 and now abandoned.

BACKGROUND OF THE INVENTION

Disposable diapers have become an accepted substitute for cloth diapers and several different constructions have achieved significant market penetration. Many of the disposable diaper configurations are rectangular and flat, and comprise sheets which are fitted to a baby from a flat state. In some instances the diaper may incorporate a geometrical folding for shape. Two very serious drawbacks with prior art disposable diapers have been the problems of fit, both around the legs and around the waist of the infant, as well as the strength of the diaper in the area where it is secured about the infant.

In solving these problems with disposable diapers, because of the nature of the product, the economics are of primary importance. The problem of fit is easily and simply solved merely by making marginal portions of the diaper elastic to improve the conformability about the legs of the infant and/or the waist of the infant. The problems of reinforcing the edge or corners of the diaper to make them stronger in their securement areas is easily and relatively simply solved by placing more layers of material in those areas. However, each of these operations will increase the complexity of the manufacture of the diaper and increase the cost of raw materials used in the diaper and hence substantially increase the ultimate cost of the diaper.

For enhanced fit, in the recent past disposable diapers with contractable side flaps which gather the side margins of a diaper have been introduced into the marketplace. Such diapers are similar to conventional moisture-impermeable panties and tend to improve the fit of the diaper about the legs of the wearer, yet are costly to manufacture. A diaper of this general type is described in U.S. Pat. No. 3,860,003.

There are also a number of patents which disclose means for making the waist band of disposable diapers elastic to improve the fit of the diaper about the waist of the wearer, for example, as shown and described in U.S. Pat. No. 3,995,637 and 3,995,640.

Also, various methods for incorporating elastic members in garments to make portions of the garments stretchable are well known in the art. Such methods include the use of heat-shrinkable or heat-recoverable film ribbons which are incorporated into the garments while in a non-elastic state and then treated with heat to provide the ribbons with elastic properties or to accentuate the elastic properties already present in the ribbons. Such techniques are generally described in U.S. Pat. Nos. 3,245,407 and 3,639,917.

Disposable diapers originally were secured with pins, but in recent times have been secured with pressure-sensitive adhesive tape fasteners or tabs. In both instances it is primarily the corners of the diapers which take the stress in securing the diaper to an infant and continue to absorb stress during the infant's active periods. The adhesive tabs are normally attached at one end thereof at the side margins of the diaper and are secured to the relatively thin backing sheet of the diaper. Since the stress is greatest in these areas, it has been known to reinforce these areas by various techniques, for example, by the use of a scrim adhered to the area, such as is disclosed in U.S. Pat. No. 3,867,940, or by thickening the backing sheet in the area of attachment as illustrated in U.S. Pat. No. 3,783,871. In either case registry problems are encountered during high-speed manufacture.

SUMMARY OF THE INVENTION

We have discovered a new and improved disposable diaper which has improved fit and at the same time provides reinforced corner areas for enhanced securement of the diaper about the waist of the infant. Further, our new diaper is economical to produce, with a minimum of extra manufacturing operations, and may be readily produced on high-speed equipment with good productivity.

In accordance with the present invention, our new and improved diaper has at least one margin having an elongated, inherently elastic ribbon member secured thereto. The elastic ribbon member is secured in the central portion and at one or both ends. The ribbon member provides an elastic region at a central portion of the margin and a unitary, relatively inelastic reinforced region in a corner portion of the diaper. In a preferred embodiment of the diaper of the present invention, each longitudinal side margin of the diaper is provided with the ribbon member. In another preferred embodiment, as additional ribbon member is provided along one or both transverse end margins of the diaper.

Preferably, the ribbon member is a strip of film which is of a width of about $\frac{1}{8}$" to 1" or more. The strip is intermittently secured to the backing and/or facing in the central portion of the diaper margin to maintain its elasticity; however, the end portions of the strip are continuously, preferably totally (i.e., over substantially the entire surface area of the end portions), secured at the corner portions of the diaper whereby the previously elastic end portions of the strip are effectively rendered inelastic, and the strip reinforces the diaper in such regions. Two other advantages emanate from the present invention. First, all of the elastic region retains full elastic function. Secondly, there is great uniformity of elasticity throughout the elastic region. These advantages provide better conformity about the leg of the infant and even distribution of force by the elastic on the leg, thus reducing skin marks or irritation to the skin of the infant. In a thermoplastic film strip the end portions may be rendered effectively inelastic by applying heat or other bonding energy to the desired area of attachment. The elastic property in the unbonded portion or portions of the film, of course, remains undisturbed. It is a relatively simple operation to take a continuous, pre-stretched length of an elastic film ribbon and adhere selected regions thereof to the standard impervious backing of a diaper during diaper manufacture.

Another equally simple technique is to attach to the diaper margin a heat-shrinkable film ribbon which becomes elastic and contracts on heating to a predetermined temperature. Such a film ribbon, while in the inelastic state, may be secured at end portions thereof along a diaper margin to the impervious diaper backing. The central portion of the ribbon is heat-treated (e.g., with a hot air blast) to shrink the central portion and impart elasticity thereto.

The foregoing expedients simultaneously produce a diaper having both improved fit and reinforced corner areas for enhanced securement of the diaper about the infant.

BRIEF DESCRIPTION OF THE DRAWINGS

FIG. 1 is a perspective view illustrating a disposable diaper embodying the present invention;

FIG. 2 is an exploded perspective view showing relative positioning of diaper elements during manufacture of the diaper depicted in FIG. 1;

FIG. 3 is a perspective view of another embodiment of the disposable diaper of the present invention;

FIG. 4 is a perspective view showing still another embodiment of the disposable diaper of the present invention;

FIG. 5 is a plan view of one embodiment of a disposable diaper of this invention with a portion broken away to show interior detail;

FIG. 6 is an enlarged cross-sectional view taken along line 6—6 of FIG. 5;

FIG. 7 is an enlarged cross-sectional view taken along line 7—7 of FIG. 5;

FIG. 8 is a plan view of another embodiment of a disposable diaper of this invention with a portion broken away to show interior detail;

FIG. 9 is a plan view of still a further embodiment of a disposable diaper of this invention with a portion broken away to show interior detail;

FIG. 10 is a plan view of an additional embodiment of a disposable diaper of this invention with a portion broken away to show interior detail;

DESCRIPTION OF THE PREFERRED EMBODIMENTS

Figure 11:
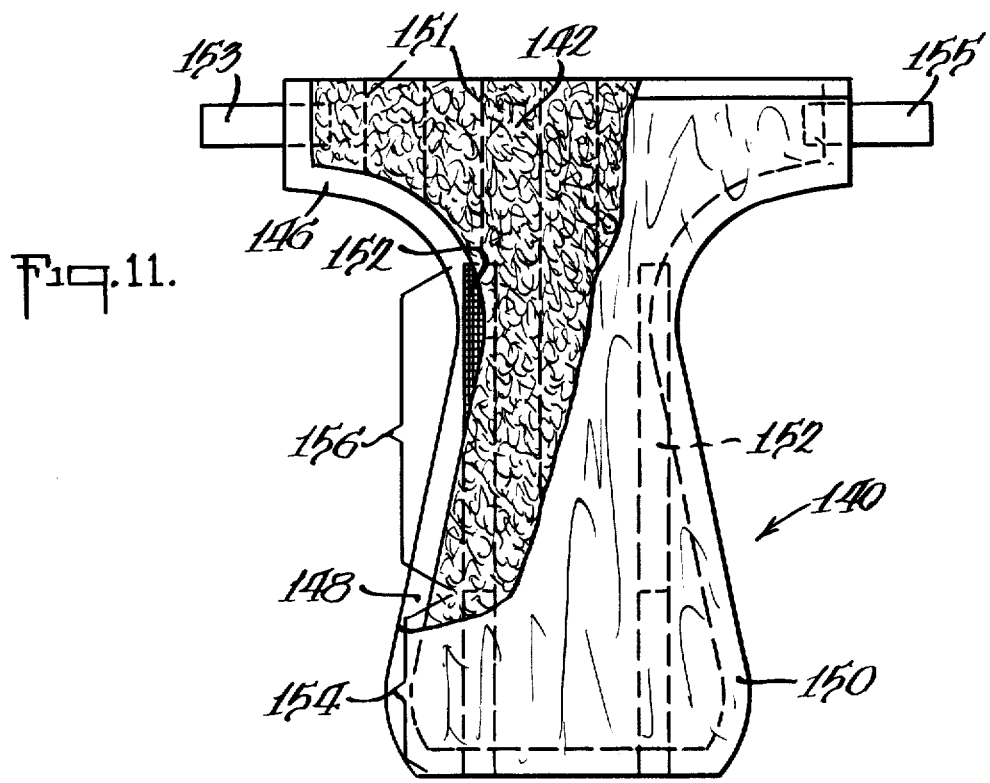
FIG. 11 is a plan view of another embodiment of a disposable diaper of this invention with a portion broken away to show interior detail.

In one preferred embodiment of the disposable diaper of the present invention, the elastic means and reinforcing means is a member which is elastic in its original state and may be relaxed or have its elasticity rendered ineffective in selected portions by heat sealing or ultrasonically sealing those portions to the diaper backing and/or facing. Many thermoplastic films are well known in the art which have this property, and are described in detail hereafter.

The term "elastic" as used herein, refers to sheets, films, ribbons and the like which have a recovery of at least 90%, when elongated to within 10% of their yield point and measured in accordance with the following formula:

$$\text{Percent retraction} = (L_e - L_t)/(L_e - L_o) \times 100$$

where
$L_o$ = original length of sample
$L_e$ = fully extended length
$L_t$ = length of sample measured 3 seconds after released from extended length.

The member used should have a width of at least ¼ inch in the areas of the diaper where it is to be used as a reinforcing means. It is preferred that the entire length of the member be at least ¼" wide and preferably ⅜" to 1" wide. The thickness of the member may vary from about ½ mil to 10 mils and its preferably between about ½ and 5 mils.

The elastic means has a recovery at 50% elongation after 3 seconds and preferably instanteously of at least about 90% and preferably close to 100%. For ease of stretchability, the modulus of elasticity of the elastic means at 50% elongation should not exceed about 2,000 lbs. per square inch.

The modulus of elasticity is preferably substantially less than 2000 pounds per square inch, and most preferably is about 20 to about 200 pounds per square inch. The elastic means may be used along both longitudinal side margins of a disposable diaper and/or along one or both front and back end portions of the diaper as desired.

Referring to FIG. 1, a disposable diaper 20 embodying the present invention is provided with longitudinal side margins 21 and 22. The central portions 23 and 24 of each side margin is elastic to provide improved fit about baby's thighs. At both ends of each longitudinal side margins are non-elastic, reinforced corners 25, 26, 27, and 28. The elastic means in each of the longitudinal side margins is a relatively wide, thin elastic film ribbon. The film ribbon has been relaxed and its elasticity removed, i.e. "killed", at both ends of the ribbon to reinforce the corners. The diaper additionally includes a first outer layer, or backing, made of a moisture-impermeable web, a generally rectangular absorbent batt positioned in superimposed relationship with respect to the backing and a second outer layer, or facing, made of a moisture-permeable web and positioned in superposed relationship to the absorbent batt. For securement about a baby, the diaper is provided with pressure-sensitive tape tabs 32 and 33. The elastic members are generally parallel to the longitudinal side margins of the batt. The ends are treated to remove elasticity so that when the diaper is relaxed the central portion of each side margin contracts and is elastic while the four corners are non-elastic but are reinforced with additional film material.

The individual components of a disposable diaper are illustrated in FIG. 2. Absorbent batt 35 is superposed over the thermoplastic film backing 36 and secured thereto by a series of glue lines 37 deposited on the backing. The absorbent batt is of smaller area than the backing and when substantially centered on the backing is spaced from the longitudinal sides as well as from the transverse ends of a diaper. The absorbent batt is flanked on its longitudinal sides by members 38 and 39 which in an extended state are secured to the backing by means of an adhesive, sonic sealing or other convenient means. Moisture-pervious facing 40 is superposed over the absorbent batt and is larger in area than the batt and is secured to the backing usually by means of the exposed end portions of the glue lines; however, other securement means may be utilized if desired. It should be noted that the elastic film members may be secured to either the backing or facing or both as desired.

In the manufacture of the diaper, only the central portions 41 and 42 of the elastic film members are allowed to remain elastic. This may be accomplished when using sonic sealing by sealing intermittently and/or in a pattern. The end portions 43 are treated with heat, ultrasonics, or similar energy inducing means, to remove the elasticity of the film in those areas.

FIG. 3 shows a disposable diaper 44 similar to the disposable diaper depicted in FIG. 1 with the exception that the elastic means and reinforcing means are in the back waist or end portion 45 of the diaper to provide improved fit about the baby's waist. The elastic means and reinforcing means in this diaper is similar to that described in regard to FIG. 1 and is a film ribbon treated as previously described so as to perform in the same manner, i.e., the central portion 46 of the end portion is elastic while the two back corners 47 and 48 are reinforced.

FIG. 4 shows yet another disposable diaper 51 similar to the disposable diapers in FIGS. 1 and 3, with the exception that all four edge portions, that is, the two longitudinal side margins 52 and 53 and the front 54 and 55 end margins, all have film ribbon members inserted therein with the central portions thereof elastic. In this embodiment the four corners, 56, 57, 58 and 59, are doubly reinforced by the overlapping of the relaxed end portions of each film ribbon member.

In the embodiment shown in FIG. 5 a disposable diaper 60 is provided with a substantially rectangular batt 61 or panel having rectilinear sides sandwiched between a backing 62 and a facing 63 and together with the backing and facing define diaper side margins 64 and 65. Curvilinear cutouts are provided in the respective central portions of the side margins of the facing and backing for further fit enhancement. Pre-stretched elastic ribbons 68 are positioned in the longitudinal side margins and are secured to the backing and facing along the longitudinal sides of the absorbent panel. The elastic ribbons have been relaxed at each end 69 and 70 to provide reinforcing areas. Glue lines 71 secure the facing and absorbent panel to the backing and adhesive tape tabs 72 and 73 provide diaper securement means. The adhesive tape tabs overlap the relaxed reinforcing areas of the ribbon to provide this area, which absorbs the most stress in use, with extra material to improve the strength of this area.

Referring to FIG. 6, which is a cross-sectional view taken along line 6—6 of FIG. 5, there is shown the impervious backing member 62 with the elastic ribbon 68 sealed to the backing member. The ribbon is sealed along two sinuous line portions 74 and 75 to the backing member, and the facing layer in the central portion as shown in FIG. 5.

As seen in FIG. 7, which is another cross-section view at the corner of the diaper, the adhesive tape tab 72 attached to the backing member 62 is also attached to the facing member 63. The tape tab area is reinforced with the non-elastic reinforcement portion 69 of member 68.

In the embodiment shown in FIG. 8, the disposable diaper 80 is provided with the absorbent batt 81 also having curvilinear side cutouts and sandwiched between a facing 82 and a backing 83 having similar cutouts. Glue lines 84 serve to secure the batt and facing to the backing. Wide elastic ribbons 85 are situated in the general rectilinear diaper side margins. The elastic ribbons extend the entire length of the diaper side margin and are intermittently secured to the backing and facing at the central portion 86 thereof to provide the desired elasticity. In the outer portions 87 and 88 the elastic ribbon has been relaxed and made non-elastic. Protruding portions 89 and 90 of the absorbent batt overlap the entire width of the relaxed ribbons to provide additional absorbent capacity. The tape tabs 91 and 92 overlap the reinforced ends of the relaxed elastic member and are reinforced thereby. The tabs provide the means for securing the diaper to the baby.

In the embodiment shown in FIG. 9, the disposable diaper 100 of the present invention comprises an impervious backing member 101 and an hourglass shaped absorbent pad 102 being narrow in the crotch area 103 of the diaper, and a top facing layer 104. In this configuration the top layer and impervious backing member form areas 105 and 106 as part of the side margins. These areas of the side margins contain no absorbent core material. This reduces the bulk of material between the baby's legs. In each side margin of the diaper, there is inserted between the impervious backing and pervious facing layer the elastic member 109 which has its central portion 110 elastic and its two end portions 111 and 112 relaxed or made non-elastic for reinforcement.

The diaper has an hourglass shaped absorbent body wherein the absorbent body in the waist portion is wider than the absorbent body in the crotch area. At the back waist portion of the diaper are adhesive tape tabs 113 and 114 which have been adhered to the portion of the backing member which is reinforced.

The embodiment shown in FIG. 10 is a disposable diaper 120 that comprises a rectangular impervious backing member 121 with a smaller area of absorbent core 122 adhered thereto with glue lines applied to the backing member. On top of the absorbent core is the facing member 124 which is coextensive with the backing member to form the longitudinal side margins 125 and 126 and the end margins 127 and 128.

Adhered between the backing and facing members at the back waist margin 127 is the member 129. The member is elastic in the central portion 130 and has been relaxed and made non-elastic at the two edge portions 131 and 32. A similar elastic member also may be inserted at the front waist portion 128 of the diaper. Adhesive tape tabs 133 and 134 are adhered to the backing member in the reinforced portion thereof and are used for securement about the baby.

In the embodiment shown in FIG. 11, the disposable diaper 140 is provided with an absorbent batt 142 having the same shape as and being sandwiched between a facing 144 and a backing 146. The backing 146 and the facing 144 are secured to each other in the margins 148 and 150. The absorbent batt 142 is provided with embossed lines 151 to assist the wicking of the urine. Elastic ribbons 152 are situated in the diaper 140 so as to be substantially within the margins 148 and 150 in the central portion of the diaper. At the rear portion 154 of the diaper, the elastic ribbons 152 are between the backing 146 and the absorbent batt 142. The elastic is secured in both the central portion 156 and the rear portion 154, however the elastic ribbon portions in the rear portion 154 are relatively inelastic and provide reinforced portions in the region where the tape tabs 153 and 155 are secured when placing the diaper on an infant.

Figure 12:
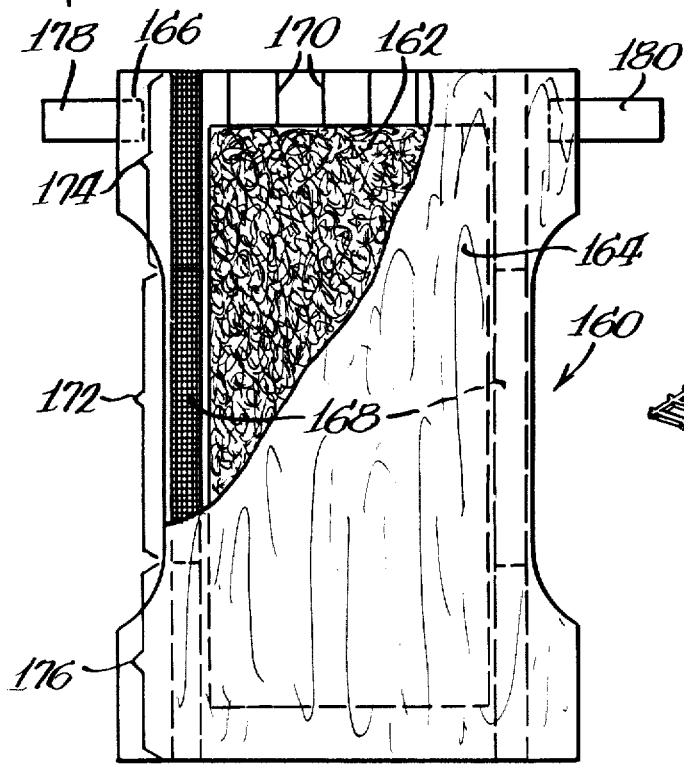
FIG. 12 is a plan view of a still further embodiment of a disposable diaper of this invention with a portion broken away to show interior detail.

FIG. 12 depicts a typical reticulated elastic 158 suitable for use in either the side or end portions of a disposable diaper.

Figure 13:
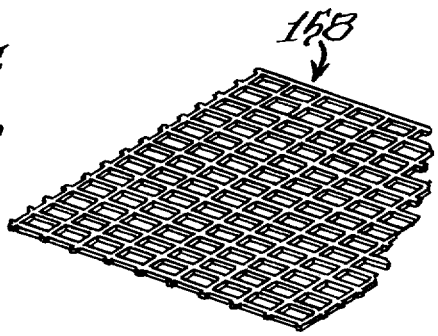
FIG. 13 is a plan view of one kind of elastic suitable for use in a disposable diaper of this invention.

In the embodiment shown in FIG. 13, the disposable diaper 160 is provided with an absorbent batt 162 of substantially rectangular shape, sandwiched between a facing 164 and a backing 166. Reticulated elastic ribbons 168 are placed between the backing and the facing. The backing and the facing are secured to each other thus securing the elastic ribbons through the apertures, by use of glue lines 170. The glue lines 170 also adhere the backing to the absorbent batt. The elastic ribbons 168 are secured in a stretched state in the central portion 172 and the rear portion 174. The elastic may or may not be secured in the front portion 176. If the elastic is secured in the front portion then both the front portion 176 and the rear portion 174 of the elastic ribbons are rendered relatively inelastic. The central portion 172 remains elastic and thus gathers the edge of the diaper in the central region. The secured inelastic regions provide reinforced corner portions so that the tape tabs 178 and 180 do not easily tear from the corner portions.

Elastic members that lose their elasticity on heat sealing and suitable for use in the diapers contemplated herein are films extruded or otherwise formed to the desired thickness utilizing unvulcanized, thermoplastic compositions which are made using an elastomeric component and an optional compatible modifier which is a thermoplastic polymer of a relatively low molecular weight but solid at ambient temperature.

Illustrative of the elastomeric components suitable for present purposes are block copolymers which comprise terminal thermoplastic polymer blocks and at least nonterminal or intermediate elastomeric polymeric polymer block. Block copolymers of this general type may be prepared using a step-wise polymerization initiator, e.g., an organolithium compound. Such block polymerization techniques are well known in the art.

The elastic component can be linear or radial $A^1$-B-$A^2$ block copolymers or mixtures thereof with simple $A^1$-B block copolymers where $A^1$ and $A^2$ can be alike or different and represent a thermoplastic polymer block, such as poly (vinyl arene) block, and B represents an elastomeric polymer block such as a conjugated diene or a lower (i.e., $C_1$–$C_4$) alkene. The modifier component is a low molecular weight thermoplastic polymer having an average molecular weight of about 500 to 7,500 and is present in the composition in an amount of about zero to about 200 parts by weight per 100 parts by weight of the elastomeric component.

A preferred thermoplastic film composition for the elastic film members comprises an elastomeric component which contains, as a major constituent thereof, an unvulcanized linear block copolymer of the general configuration $$A^1\text{-B-}A^2$$

wherein $A^1$, $A^2$, and B have the same meaning as hereinabove. In these block copolymers the A-blocks are derived from styrene or styrene homologues, and the B-blocks are derived from conjugated dienes or lower alkenes. The thermoplastic polymer modifier is compatible with the elastomeric component and associates principally with the thermoplastic terminal blocks of the aforesaid unvulcanized block copolymer. The thermoplastic polymer modifier preferably has an average molecular weight of about 1000 to about 3000, and is present in the film composition in an amount of about 80 to 200 parts by weight per 100 parts by weight of the elastomeric component.

The preferred $A^1$-B-$A^2$ block copolymers have A-blocks derived, i.e., polymerized or copolymerized, from styrene or styrene homologues; and B-blocks derived from conjugated dienes, such as isoprene or butadiene, or from lower alkenes, such as ethylene and butylene. Small proportions of other monomers also may enter into the block copolymers themselves. The individual A-blocks can have an average molecular weight of at least about 6000, preferably in the range of about 8000-30,000 and the A-blocks constitute about 5-50 percent, preferably about 10-30%, by weight of the B-blocks for linear $A^1$-B-$A^2$ block copolymers preferably is in the range of about 45,000-180,000 and that of the linear copolymer, itself, preferably is in the range of about 75,000-200,000. The average molecular weight of the radial $A^1$-B-$A^2$ block copolymers preferably is in the range of about 125,000-400,000. The term "linear block copolymer" (or copolymers) includes branched $A^1$-B-$A^2$ copolymers as well as unbranched $A^1$-B-$A^2$ copolymers.

The radial $A^1$-B-$A^2$ copolymers useful for manufacture of elastic members for diapers of this invention are of the type described in U.S. Pat. No. 3,281,383 to Zelinski et al and conform to the following general formula: $(A\text{-B-}_nX)$, wherein A is a thermoplastic block polymerized from styrene or styrene homologues, B is an elastomeric block derived from conjugated dienes or lower alkenes, as indicated above, X is an organic or inorganic connecting molecule, with a functionality of about 2 to 4 as described in U.S. Pat. No. 3,281,383, or possibly with a higher functionality as described in the Article entitled "New Rubber is Backed by Stars". appearing on page 35 of the June 11, 1975, issue of Chemical Week. As used hereinabove, "n" has a value corresponding to the functionality of X. Another suitable elastomeric component is elastomers wherein the sheet material contains thermoplastic rubber and amorphous polypropylene. The thermoplastic rubbers are block copolymers having blocks of polybutadiene or polyisoprene, and blocks of polystyrene. A review articlediscussing these materials is "Structure And Properties Of Block Polymers And Multi-phase Polymer Systems: An Overview Of Present Status And Future Potential", by S. L. Aggarwal, *Polymer*, Vol. 17, November 1976, pages 938-956. Two representative types of thermoplastic rubbers are the linear block copolymers (A-B-A) having a mid-block of polybutadiene or polyisoprene and end-blocks of polystyrene, and the "star" or "radial" block copolymers having from 4 to 20 "arms" connected to a common center. Each arm is an A-B block copolymer, the inner portion being polybutadiene or polyisoprene, with the outer portion being polystyrene.

The typical thermoplastic rubber contains discrete polystyrene domains in a rubbery matrix. Apparently the polystyrene domains act in a manner analogous to conventional chemical cross links. The resulting rubber acts as though it has been vulcanized, even though no chemical crosslinks are present.

When the thermoplastic rubber is heated to about 200° F., the polystyrene domains begin to soften, and at temperatures of the order of 300° F. to 400° F., the thermoplastic rubbers can be melt processed by mechanical working in a manner analogous to conventional thermoplastic compositions. Upon cooling, the discrete polystyrene domains are reformed, and the material again exhibits rubbery elastomeric properties.

While thermoplastic rubbers can be processed in ways analogous to those used for conventional thermoplastic polymers, for the reasons discussed above, it has been found to be impracticably difficult to extrude pure thermoplastic rubber into thin films.

The material that is used to improve the processability of thermoplastic rubber, while still retaining the characteristic rubbery properties of the rubber, is amorphous polypropylene. Amorphous polypropylene is a known material. It is essentially atactic polypropylene having an isotactic content of not more than about 20 weight percent, and preferably not more than about 10 weight percent.

The amorphous polypropylene is employed in an amount sufficient to improve the processability of the thermoplastic rubber when extruding thin films or sheets. Such improvement is evidenced by the ability to draw down extruded webs of the rubber/amorphous polypropylene mixture to thereby produce sheets or films having thicknesses less than the die gap. Further, the pressure in the extruder and die is greatly reduced, which permits more economical operation. The exact minimum amount of amorphous polypropylene varies somewhat from case to case, but it is usually of the order of about 10 weight percent, based on weight of rubber plus amorphous polypropylene, although the proportion may be as low as about 5 weight percent (on the same basis) in some cases. The upper limit of polypropylene will also vary from case to case, depending on the nature of the ingredients and the use intended for the product. At proportions above about 35 weight percent (on the same basis), a significant reduction in the characteristic rubbery elastomeric properties of the product begins to occur. This may be acceptable for some uses, and not for others. Thus, the upper limit of amorphous polypropylene would be that point at which the product still retains significant rubbery elastomeric characteristics.

Other conventional materials, employed in the usual amounts, can be employed in the mixture for their known purposes. Such materials include pigments, anti-blocking agents, stabilizers, anti-oxidants, ultraviolet stabilizers, bonding aid, and the like. The film may be extruded in such a manner so as to provide a reticulated film.

The preferred elastic film member is highly thermoplastic and, though elastomeric, is unlike rubber in that the film exhibits a relatively sharp melting point and is capable of being heat shaped. Also, the elastic film member can form permanent heat seals to substrates such as non-woven fabrics, or the like, at relatively low heat sealing temperatures, generally not above about 350° F. The film member is highly elastic and has relatively low rubber modulus, i.e., it exhibits in at least one direction an elastic recovery from 50 percent stretch to at least 75 percent, preferably at least about 80 percent, and a 50 percent rubber modulus of not above about 2000 pounds per square inch, preferably in the range of about 20 to about 200 pounds per square inch at 50 percent elongation. The film member also is very flexible, extensive and soft and normally exhibits a Gurley stiffness of about one or less at a film thickness of one mil, and an elongation to break of at least about 300%, preferably at least about 400%, in at least one direction at ambient temperature.

In some embodiments of the disposable diaper of the present invention, the elastic means and reinforcing means is a member which may be made elastic by imparting heat or other forms of energy to the member to shrink the member and provide it with elastic characteristics. A portion of the member is so treated to provide the elastic means while other portions are not treated and provide the reinforcing means.

The heat shrinkable films which may be used as elastic members in the disposable diapers of the present invention may be the polyolefin films which have been oriented to a degree and which will then become elastic when heat shrunk. Usually, a preferred technique for orienting the polyethylene film to provide the heat shrunk elastic properties is by irradiation such as suggested in British Pat. No. 866,820. Also, useful as the heat shrunk elastic members are the copolymers of ethylene and vinyl acetate, ethylene and ethyl acrylate, and the like. The forming of such copolymers is well known and specific methods of forming such materials are disclosed in U.S. Pat. Nos. 2,200,429 and 2,953,551. After the copolymer is formed and made into a film, it is given the proper orientation as described in the previously-mentioned British Pat. No. 866,820.

The elastic film may be continuous or may be reticulated having apertures of varying sizes and shapes.

Several different types of facing materials may be used for the diaper facing, for example, the facing may be a non-woven web made of a mixture of fibers consisting predominantly of short, cellulosic fibers such as wood pulp fibers or cotton linters in amounts of 75% to about 98%, the balance being textile length fibers such as rayon as described in U.S. Pat. No. 3,633,348 to Liloia et al.

Non-woven facing materials suitable for use in disposable diapers of this invention can have fabric weights in the range of from about 0.5 to 5 ounces per square yard and densities of less than 0.15 grams/cc., generally in the range of about 0.05 to 0.1 gram/cc. The dry strength of the facing sheet for fabric having a weight of about 0.15 ounces per square yard is at least 0.15 lbs. per inch of width in the machine direction. Such fabrics have good elongation, loft, softness and drape characteristics. Facings may also be made of an apertured non-woven fabric which is formed, for example, in accordance with the teachings of commonly assigned U.S. Pat. Nos. 2,862,251; 3,081,514; and 3,081,515. Briefly, such fabrics are foraminous structures wherein groups of fibers have been rearranged from a non-woven starting web to positions surrounding less dense fabric portions by passage of fluid through the starting material. The fibers within the groupings are interlocked and may be arranged in various patterns as is well known in the art. These fibers can be made of naturally occurring fibers, synthetic fibers or blends thereof. Typical facing sheets made of polyester type fibers may have a weight of about 0.75 ounces per square yard.

The facings may be the same size as, and coterminous with the backing; or alternatively, the facing may be wider than the backing and have its side edges inwardly folded so that the facing is coterminous with the backing, as is shown in FIG. 3 of U.S. Pat. No. 3,612,055. In the latter case, the elastic members may be secured above the inwardly folded side edges of the facing. In addition, facings can be formed of non-apertured materials such as non-woven isotropic webs or apertured polyolefin or polyester films having the desired moisture permeability. In all of the aforementioned facings, the material should be relatively hydrophobic so as to retard wicking within the facing.

The moisture absorbent batt or panel of a desired shape, but smaller than the facing and the backing, can be formed in accordance with the teachings of U.S. Pat. No. 3,612,055 to Mesek, et al.

A suitable backing material for the diapers embodied in the present invention can be an opaque polyolefin, for example, polyethylene about 0.001" thick. Another suitable material for this purpose is a polyethylene terephthalate having a thickness of about 0.0005".

Perhaps the simplest and easiest way of adhering the elastic film member to the film and facing along the longitudinal side portion of the diaper is to ultrasonically weld it in or weld the various layers together using ultrasonic welding equipment such as that sold by the Branson Sonic Power Company. Two possible method variations may be used for ultrasonically welding the member to the diaper. In the first method the central portion of the elastic film is sonically sealed in an intermittent pattern, and the end portions heat sealed throughout their area. In the second method the entire film member is sonically sealed with high energy applied to the end portions to seal their entire surface. In both techniques the film is heated at its end portions to a point where it almost melts and loses substantially all of its memory and is thus non-elastic in those areas. The elastic member may be ultrasonically welded to the backing and/or the facing as desired or in the case of a reticulated film, the facing and backing are welded through the film apertures.

While the elastic film members described above are in the form of members which lose their elasticity upon the application of heat or other energy, the present invention is not limited thereto, and members which become elastic upon the application of heat or other energy may also be used. Films which shrink and become elastic when heated are well known and may be used to produce diapers in accordance with the present invention. Such a heat shrinkable film member may be inserted in a diaper margin and a portion of the member adhered to the diaper as by gluing. Another portion of the member is intermittently secured to the diaper. Upon the application of heat or other energy to the intermittently secured portion, the portion shrinks and becomes elastic. The adhered glued portion remains in place and acts to reinforce the diaper in that area.

The foregoing description and the drawings are illustrative and are not to be taken as limiting. Still other variations and modifications are possible without departing from the spirit and scope of the present invention.

We claim:

1. A method for forming a conformable garment having one or more discrete elasticized areas, said method comprising:
   (a) providing a garment component having a central portion defined between two end portions;
   (b) stretching at least one ribbon of thermoplastic elastomeric material;
   (c) subjecting at least one discrete portion of said stretched ribbon to heat so as to "kill" the elastic properties thereof in each heated portion while leaving the elastic properties of each unheated portion unaltered;
   (d) before, during, or after step (c), securing at least part of the stretched ribbon to said garment component substantially end-to-end of the garment component with one heated portion of the ribbon secured in an end portion of said garment component and with an unheated portion of the ribbon secured to the central portion of said garment component whereby, when said ribbon is permitted to contract with said garment component, said garment component central portion is elasticized to gather while at least one end portion of said garment component remains inelastic and ungathered.

2. The method in accordance with claim 1 in which step (d) includes bonding said ribbon to said garment component.

3. The method in accordance with claim 1 in which step (d) includes securing said one heated portion of the ribbon to said garment component end portion at spaced locations along said garment component end portion.

4. The method in accordance with claim 1 in which step (d) includes securing said one heated portion of the ribbon to said garment component end portion substantially continuously along said garment component end portion.

5. The method in accordance with claim 1 in which step (d) includes securing said one heated portion of the ribbon at the distal end of said garment component end portion.

6. The method in accordance with claim 1 in which step (c) includes subjecting at least two spaced-apart discrete portions of said ribbon to heat so as to "kill" the elastic properties thereof in each heated portion while leaving unaltered the elastic properties of each unheated portion between said two spaced-apart discrete portions and in which step (d) includes (1) securing one of said two spaced-apart unheated portions of said ribbon to one end of said garment component and (2) securing the other of said two spaced-apart unheated portions of said ribbon to the other end of said garment component.

7. The method in accordance with claim 1 in which step (a) includes providing said garment component as a diaper sheet material in which said central portion is a crotch portion of the diaper sheet material and in which each said end portion is a waistband portion of the diaper sheet material.

8. The method in accordance with claim 1 in which step (a) includes initially providing said garment component in a continuous web and in which step (b) includes initially providing said ribbon in a continuous length.

9. A method for forming an elasticized disposable diaper having (1) at least one layer of sheet material with a central portion defined between to end portions and (2) thermoplastic ribbons of elastomeric material attached lengthwise along opposite edges of the central portion of said sheet material in a manner in which said ribbons apply a gathering force in the central portion thereof, said method including rendering end portions of said ribbons effectively inelastic by the application of heat to said ribbon end portions when stretched, and said method including securing each said ribbon end portion to substantially the entire length of an end portion of said layer of sheet material before, during, or after said application of heat.

10. The method in accordance with claim 9 in which said step of securing each said ribbon end portion includes securing one said ribbon end portion to substantially the entire length of an end portion of the layer of sheet material at spaced locations along substantially the entire length of the end portion of the layer of sheet material.

* * * * *